United States Patent [19]

Sach

[11] Patent Number: 4,665,078
[45] Date of Patent: May 12, 1987

[54] 2-(3-AMINO-5-HALO-2-PYRIDYLALK-YLAMINO)-PYRIMIDONES USEFUL AS HISTAMINE H1-ANTAGONISTS

[75] Inventor: George S. Sach, Welwyn, England

[73] Assignee: Smith Kline & French Laboratories Limited, Welwyn Garden City, England

[21] Appl. No.: 629,661

[22] Filed: Jul. 11, 1984

[30] Foreign Application Priority Data

Jul. 23, 1983 [GB] United Kingdom ............... 8319874

[51] Int. Cl.$^4$ ................... A61K 31/505; C07D 239/36
[52] U.S. Cl. .................................... 514/272; 544/320; 546/256
[58] Field of Search ..................... 544/320; 514/272

[56] References Cited

U.S. PATENT DOCUMENTS 4,154,834 5/1979 Brown et al. ................... 544/310

OTHER PUBLICATIONS

Sach, Chem. Abst. 101:171108Z, eq. EP 112142.
Sach, Chem. Abst. 101:191953Z eq. EP 107914.
Adger et al, Chem. Abst. 102:95545t eq. EP 122109.
Sach, Chem. Abst. 99:22483f, eq. EP 68833.
Derwent Abstract 05126K (EP 68,833 Jan. 5, 1983).
Derwent Abstract 05127K (EP 68,834 Jan. 5, 1983).
Derwent Abstract 84–122085 (EP 107,914 May 9, 1984)
U.S. Ser. No. 537,457.
Derwent Abstract 84–160122 (EP 112,142 Jun. 26, 1984).
U.S. Ser. No. 559,520.

Primary Examiner—Donald G. Daus
Assistant Examiner—Cecilia Shen
Attorney, Agent, or Firm—Linda E. Hall; Stuart R. Suter; Alan D. Lourie

[57] ABSTRACT

The invention describes 5-halo-3-amino-2-pyridyl derivatives which are useful as histamine H$_1$-antagonists. Particular compounds described are 2-[4-(5-bromo-3-aminopyrid-2-yl)butylamino]-5-(6-methylpyrid-3-ylmethyl)-4-pyrimidone and 2-[4-(5-bromo-3-aminopyrid-2-yl)butylamino]-5-(N-oxopyrid-4-ylmethyl)-4-pyrimidone.

10 Claims, No Drawings

2-(3-AMINO-5-HALO-2-PYRIDYLALKYLAMINO)-PYRIMIDONES USEFUL AS HISTAMINE H1-ANTAGONISTS

This invention relates to certain pyrimidone derivatives, compositions containing them and their use as histamine $H_1$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. 1966, 27, 427) and the actions of histamine at these receptors are inhibited by drugs commonly called "antihistamines" (histamine $H_1$-antagonists) a common example of which is mepyramine. A second type of histamine receptor is known as the $H_2$-receptor (Black et al Nature 1972, 236, 385). The actions of histamine at these receptors are not inhibited by mepyramine but are inhibited by burimamide. Compounds which inhibit the actions of histamine at histamine $H_2$-receptors are called histamine $H_2$-antagonists.

European Patent Application No. 0068833 discloses compounds of formula (1):

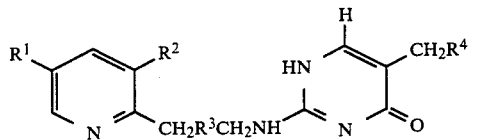

and pharmaceutically acceptable salts thereof; where
$R^1$ is halogen or nitro;
$R^2$ is $C_{1-4}$ alkyl;
$R^3$ is a $C_{1-3}$ alkylene group; and
$R^4$ is 3-pyridyl; N-oxo-3-pyridyl; 6-methyl-3-pyridyl; N-oxo-6-methyl-3-pyridyl; 6-hydroxymethyl-3-pyridyl; 4,6-dimethyl-3-pyridyl; N-oxo-4,6-dimethyl-3-pyridyl; 6-hydroxymethyl-4-methyl-3-pyridyl; 5,6-dimethyl-3-pyridyl; N-oxo-5,6-dimethyl-3-pyridyl; 6-hydroxymethyl-5-methyl-3-pyridyl; 4-pyridyl or N-oxo-4-pyridyl.

These compounds are useful as histamine $H_1$-antagonists.

A new series of pyrimidone derivatives having $H_1$-antagonist activity has now been discovered.

The compounds of this invention are useful as histamine $H_1$-antagonists, that is they are useful for the treatment of diseases for example of bronchial asthma, rhinitis, hayfever and allergic eczema whose symptoms are mediated through the action of histamine at $H_1$-receptors.

Accordingly the present invention provides compounds of formula (2):

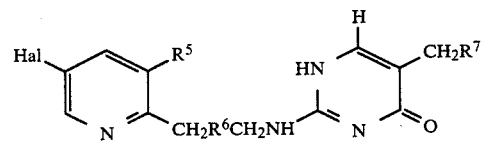

and pharmaceutically acceptable salts thereof, where
Hal is a halogen atom
$R^5$ is an amino group or a pharmaceutically acceptable derivative thereof convertible in vivo to amino;
$R^6$ is a $C_{1-3}$ alkylene group; and
$R^7$ is 3-pyridyl; N-oxo-3-pyridyl; 6-methyl-3-pyridyl; N-oxo-6-methyl-3-pyridyl; 6-hydroxymethyl-3-pyridyl; 4,6-dimethyl-3-pyridyl; N-oxo-4,6-dimethyl-3-pyridyl; 6-hydroxymethyl-4-methyl-3-pyridyl; 5,6-dimethyl-3-pyridyl; N-oxo-5,6-dimethyl-3-pyridyl; 6-hydroxymethyl-5-methyl-3-pyridyl; 4-pyridyl or N-oxo-4-pyridyl.

$R^5$ can represent amino or a pharmaceutically acceptable derivative thereof which is convertible in vivo to amino, that is derivatives which in vivo are hydrolysed or metabolised to a free amino group. Examples include $C_{1-4}$ alkylaminio for example methylamino and $C_{1-4}$ alkanoylamino for example acetamido.

Preferably $R^5$ is amino.

Hal is for example chlorine, bromine or iodine; preferably it is bromine.

By way of example —$R^6$— can be methylene, 1,2-ethanediyl, or 1,3-propanediyl.

Preferably $R^6$ is 1,2-ethanediyl.

Preferably the group $R^7$ is an optionally substituted 3-pyridyl group. Preferably one substituent occupies position 6. Thus preferably $R^7$ is 6-methylpyrid-3-yl.

Examples of compounds within the scope of this invention are:
2-[4-(5-bromo-3-aminopyrid-2-yl)butylamino]-5-(6-methylpyrid-3-ylmethyl)-4-pyrimidone;
2-[4-(5-bromo-3-aminopyrid-2-yl)butylamino]-5-(N-oxo-pyrid-4-ylmethyl)-4-pyrimidone;
and their pharmaceutically acceptable salts.

The compounds of formula (2) are shown and described as 4-pyrimidones which exist in equilibrium with the corresponding 6-one tautomers. These compounds also exist to a lesser extent as the hydroxy tautomers, and the pyrimidine ring may also exist in the following tautomeric forms:

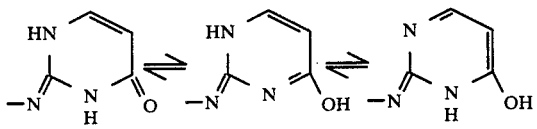

It will be understood that all these tautomeric forms are within the scope of the present invention.

The compounds of formula (2) form pharmaceutically acceptable salts with pharmaceutically acceptable salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

The compounds of this invention can be made by a process which comprises reacting a compound of formula (3):

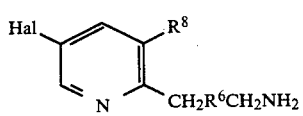

or a salt thereof, where Hal and $R^6$ are as defined with reference to formula (2) and $R^8$ is amino or a protected amino group with a compound of formula (4):

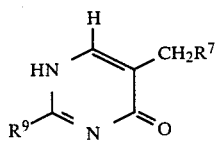

(4)

where R⁷ is as defined with reference to formula (2) and R⁹ is a group displaceable with amine, thereafter where R⁷ is N-oxo-6-methyl-3-pyridyl; N-oxo-4,6-dimethyl-3-pyridyl; or N-oxo-5,6-dimethyl-3-pyridyl; converting the compound of formula (2) so obtained into the corresponding compound of formula (2) where R⁷ is 6-hydroxymethyl-3-pyridyl; 6-hydroxymethyl-4-methyl-3-pyridyl; or 6-hydroxymethyl-5-methyl-3-pyridyl; where necessary converting the group R⁸ into a group R⁵ and optionally converting the compound of formula (2) so obtained into a pharmaceutically acceptable salt.

In the protected amino group R⁸, the protecting group can be any group stable under the reaction conditions and used routinely for the protection of an amino group. For example it can be $C_{1-4}$ alkyl, $C_{1-4}$ alkanoyl, benzyl or benzoyl.

These protecting groups can be introduced and removed by standard methods.

Where the protecting group is also a group which is convertible in vivo to amino then it is not necessary to remove it unless the free amino compound is required. Where the protecting group is one which is either not pharmaceutically acceptable or not convertible in vivo to amino then it is removed and optionally the free amino group can be converted into a derivative which is.

The compounds of formula (2) where R⁷ is N-oxo-6-methyl-3-pyridyl; N-oxo-4,6-dimethyl-3-pyridyl; or N-oxo-5,6-dimethyl-3-pyridyl can be converted into the corresponding compound of formula (2) where R⁷ is 6-hydroxymethyl-3-pyridyl; 6-hydroxymethyl-4-methyl-3-pyridyl; or 6-hydroxymethyl-5-methyl-3-pyridyl; by reacting with an organic anhydride for example trifluoroacetic anhydride.

Pharmaceutically acceptable salts of compounds of formula (2) can be prepared by standard methods, for example by reacting a solution of the compound of formula (2) with a solution of the acid.

Examples of groups R⁹ are $C_{1-4}$ alkylthio (particularly methylthio), benzylthio, chlorine, bromine and nitroamino. Preferably R⁹ is nitroamino.

The reaction can be carried out at an elevated temperature in the absence of a solvent, for example at from 80° to 170°, preferably from 120° to 140°, or in a solvent at an elevated temperature, for example at the reflux temperature of the reaction mixture. The choice of solvent is affected by solubility characteristics of the reactants and the nature of R⁹. Preferably the solvent is pyridine, a picoline or mixture of picolines, a $C_{1-4}$ alkanol, preferably ethanol or 1-propanol, a $C_{1-4}$ alkanol, 1,2-ethanediol, a ketone, for example acetone or 2-butanone, a high boiling alkoxyaryl ether for example anisole, or a polar aprotic solvent, for example dimethylformamide, dimethylacetamide, dimethylsulphoxide, hexamethylphosphoramide, sulpholane, acetonitrile or nitromethane.

Compounds of formula (3) can be prepared by reacting a compound of formula (5):

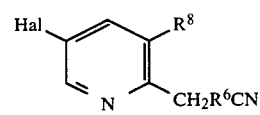

(5)

where Hal, R⁸ and R⁶ are as defined with reference to formula (3) with hydrazine in the presence of Raney nickel.

This reaction is carried out at a moderate temperature, for example from 5° C. to about 70° C. and preferably from about 10° C. to room temperature.

Compounds of formula (5) can be prepared in turn by reacting a compound of formula (6):

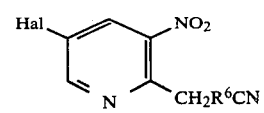

(6)

with hydrazine in the presence of a transition metal catalyst to produce a compound of formula (5) where R⁸ is amino and, if required, the amino group R⁸ can be converted into a protected amino group.

The second hydrazine reduction to prepare compounds (5) can be carried out using milder hydrogenation catalysts than Raney nickel.

An example of a mild catalyst for this step is palladium or an inert support (in particular palladium on charcoal). The temperature at which the reaction is carried out depends on the catalyst. Where a mild catalyst is employed, higher temperatures for example from 55°–70° C. may be employed. With a more powerful catalyst, for example Raney nickel, the temperature does not in practice exceed 55° C.

Preferably the reaction is carried out at from 5° C. to room temperature regardless of the catalyst.

The first or second reduction can be carried out in the presence of a solvent the choice of which is not critical to the success of the reaction provided that it is substantially inert to the reagents and product. Examples of solvents for use in this process include $C_{1-6}$ alkanols in particular methanol and ethanol.

The time for which the hydrazine reductions are allowed to proceed depends upon the nature of reagents, the temperature at which it is carried out and in the second reduction, the catalyst. The progress of the reaction can be monitored by standard techniques for example thin layer chromatography and, when the reaction has finished, the product can be isolated by standard techniques, for example removing the catalyst by filtration and evaporating the solvent.

Compounds of formula (5) where R⁸ is amino can be converted by standard methods into the corresponding compound where R⁸ is a protected amino group.

Where R⁸ in the compound of formula (3) is amino, it can be prepared by concerted one pot reaction from compounds of formula (6), that is by reacting the compound of formula (6) with sufficient hydrazine and a catalyst to form a compound of formula (5) in situ, where the catalyst for the next step is not Raney nickel, removing the catalyst (e.g. by filtration) and then adding Raney nickel and sufficient hydrazine to convert the compound of formula (5) into the corresponding compound of formula (3).

Compounds of formula (6) can be prepared by reacting a disubstituted chloropyridine of formula (7):

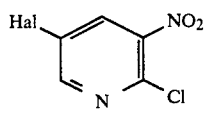

with a malonic acid ester of formula (8):

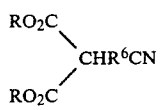

where Hal and $R^6$ are as previously defined and R is an ester forming group, in the presence of a strong base in an inert reaction medium, and thereafter de-esterifying and decarboxylating the product.

In particular the groups R can be ethyl.

In particular the strong base can be sodium hydride.

The reaction medium is one which is substantially inert to the reagents and product. In particular the medium can be dry tetrahydrofuran.

The compound of formula (7) can be made by known methods.

The compounds of formula (4):

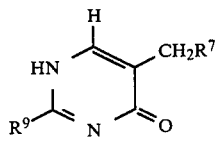

are known or can be made by analogy with known processes as disclosed in for example U.S. Pat. No. 4,154,834 and European Patent Specification No 17,679.

Compounds of formula (2) can also be prepared by reacting a guanidine of formula (9):

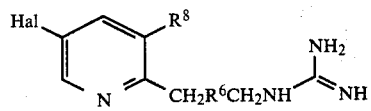

where Hal, $R^6$ and $R^8$ are as defined with reference to formula (3) with a compound of formula (10):

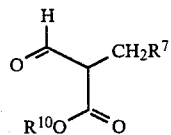

where $R^7$ is as defined with reference to formula (2) and $R^{10}$ is $C_{1-4}$ alkyl (particularly ethyl) benzyl or phenyl.

The reaction can be carried out by heating the guanidine of formula (9) with the compound of formula (10) optionally in a solvent for example an alcohol corresponding to the ester function in the compound of formula (10) that is $R^{10}OH$, at an elevated temperature, preferably in the presence of a base in particular the sodium alkoxide $NaOR^{10}$ corresponding to the ester function of the compound of formula (10).

The guanidines of formula (9) can be prepared by reacting an amine of formula (3) with a compound of formula (11):

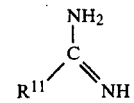

where $R^{11}$ is a leaving group for example methylthio.

The histamine $H_1$-antagonist activity of the compounds of formula (2) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases stepwise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of Examples 1 and 2 have $pA_2$ values greater than 8.

The histamine $H_2$-antagonist activity of the compounds of formula (2) can be demonstrated in vitro in the guinea pig atrium test. In this test a spontaneously beating isolated portion of the guinea pig right atrium is secured under tension (300 mg) between an anchorage and a transducer in a 15 ml tissue bath and immersed in McEwens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against Log D (the concentration of compound under test) is made and the point of intersection with the Log (DR-1) ordinate is taken as the measure of the activity ($pA_2$ value). The compounds of Examples 1 and 2 have $pA_2$ values of less than 6.

The activity of compounds of formula (2) as histamine $H_1$-antagonists can be demonstrated in vivo by the inhibition of histamine induced bronchoconstriction. Guinea pigs of either sex are anesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intranvenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist. The compounds of Examples 1 and 2 hereafter cause displacement of histamine dose-response curves with a dose-ratio of 10 at doses of less than 0.8 micromole $kg^{-1}$ i.v.

The potency of compounds of formula (2) as histamine $H_1$-antagonists and their duration of action can be demonstrated in vivo by the inhibition of histamine or histamine $H_1$-agonist induced reduction of blood pressure in the anaesthetised cat.

Cats of either sex weighing between 2 and 3 kg were starved overnight and anaesthetised with sodium pentabarbitone (60 mg/kg i.p.). The trachea was cannulated and blood pressure was measured in a femoral artery. The compound under investigation was administered by cannulae in the right and left femoral veins. Anaesthetic was administered as required into one brachial vein. Dose-response curves were constructed by administering a standard $H_1$-agonist, 2-(2-aminoethyl)pyridine in increasing dose from $10^{-8}$ mol/kg to $10^{-5}$ mol/kg. The 2-(2-aminoethyl)pyridine-induced reduction in blood pressure was measured. The effect of the antagonists can be quantified by displacement of the 2-(2-aminoethyl)pyridine dose-response curve expressed as a dose-ratio. The compounds of Examples 1 and 2 caused displacement of the dose-response curves with a dose-ratio of 10 at doses of 0.06 and 0.0058 micromole/kg respectively.

The compound 2-[4-(5-bromo-3-methylpyrid-2-yl)butylamino]-5-(6-methylpyrid-3-ylmethyl)-4-pyrimidone which is described in European Patent Application No. 0068833 causes displacement of 2-(2-aminoethyl)pyridine dose-response curve with a dose-ratio of 10 at a dose of 0.215 micromole/kg.

This test also suggests that the compounds of the Examples have a prolonged duration of action.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (1) or a pharmaceutically acceptable salt thereof and a pharmaceutically acceptable carrier.

Compounds of formula (1) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterileaqueous carrier of parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol.

Where appropriate, bronchodilators and antiasthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included in the pharmaceutical compositions.

Each dosage unit for oral administration contains preferably from 1 to 200 mg of a compound of formula (1) or a pharmaceutically acceptable salt thereof calculated as the free base.

A dosage unit for parenteral administration preferably contains from 1 to 10 mg of a compound of formula (1) or a pharmaceutically acceptable salt thereof calculated as the free base.

The invention also provides a method of blocking histamine $H_1$-receptors which comprises administering to a subject an effective amount to block said receptors of a compound of formula (1) or a pharmaceutically acceptable salt thereof.

The compounds of formula (1) and their pharmaceutically acceptable salts will normally be administered to a subject in a pharmaceutical composition as described above, for the treatment of rhinitis, hayfever, bronchial asthma or allergic eczema. Typically the daily dosage regimen for an adult patient is between 15 mg and 400 mg and preferably between 15 mg and 200 mg or an intravenous, subcutaneous or intramuscular dose of between 1 mg and 50 mg, and preferably between 1 mg and 10 mg of a compound of formula (1) or a pharmaceutically acceptable salt thereof calculated as the free base, the composition being administered 1 to 4 times per day.

The following Examples illustrate the invention.

EXAMPLES

EXAMPLE 1

(a) A mixture of concentrated sulphuric acid (35 ml) and nitric acid (35 ml) was added dropwise with stirring to a chilled (5° C.) solution of 2-amino-5-bromopyridine (50.3 g) in concentrated sulphuric acid (240 ml) maintaining the temperature of the reaction mixture at 5°–6° C. throughout the addition. When the addition was complete, the reaction mixture was stirred for a further 1.0 hr. at 5°–8° C. and then warmed to 30° C. and allowed to stand for ca 18 hr.

Further concentrated nitric acid (35 ml) was added portionwise to the reaction mixture with stirring while maintaining the temperature at 30°–40° C. A portion (50 ml) of the solution was poured into hot (ca 70° C.) water (100 ml) with rapid stirring and this mixture was heated to 120° C. Gas evolved. When the evolution of gas ceased further portions (75 ml) of the reaction mixture were added maintaining the temperature at 120° C. When the additions were completed, the solution obtained was poured into ice (1 kg) and chilled in a salt/ice bath. Fine orange crystals formed which were removed by filtration and recrystallised from dimethylformamide/water to give 2-hydroxy-3-nitro-5-bromopyridine (23.5 g) m.p. 240°–243° C.

(b) A solution of 2-hydroxy-3-nitro-5-bromopyridine (23.4 g) in phosphoryl chloride (16 ml) was heated under reflux for 2.5 hr. The reaction mixture was poured into ice/water and a brown solid was produced which was removed by filtration. The solid was dissolved in chloroform, dried (MgSO₄) and decolourised by heating with charcoal for 30 min. The solvent was evaporated from the decolourised solution to yield a yellow solid (24.0 g) which was recrystallised from ether/petroleum ether (40°–60° C.) to yield 2-chloro-3-nitro-5-bromopyridine (19.4 g) m.p. 66°–68° C.

(c) A solution of 2-(2-cyanoethyl)malonic acid diethyl ester (24.2 g) in tetrahydrofuran (15 ml) was added to a suspension of sodium hydride (2.45 g) in tetrahydrofuran (30 ml) at 20° C. under nitrogen. To this was added 2-chloro-3-nitro-5-bromopyridine (22 g) and the mixture so obtained was heated to 93°–95° C. A small amount of tetrahydrofuran was allowed to distil off. The mixture was heated under reflux for 2.5 hr. The reaction mixture was poured into water and neutralised to pH 7 with concentrated hydrochloric acid. The aqueous phase was extracted with chloroform, dried (MgSO₄) decolourised with charcoal and filtered through a silica column. The chloroform eluant was evaporated to yield an oil which slowly crystallised. The crystals were washed in petroleum ether (40°–60° C.) and dried to yield 4-(5-bromo-3-nitropyrid-2-yl)-4,4-bis(carbethoxy)butyronitrile (28 g) m.p. 58°–62° C.

(d) 4-(5-Bromo-3-nitropyrid-2-yl)-4,4-bis-(carbethoxy)butyronitrile (21.8 g) was added to a mixture of aqueous sodium hydroxide solution (1M, 263.6 ml) and methanol (635 ml). The mixture so obtained was stirred for 18 hr. The mixture was acidified to pH 1.5 by addition of concentrated hydrochloric acid and heated at 50° C. for 4.75 hr. The solution was neutralised to pH 7 with sodium hydroxide solution and the methanol removed by distillation. The aqueous solution remaining was extracted with chloroform to give an oil (11.2 g) which was chromatographed on a silica column with chloroform to give 5-bromo-3-nitro-2-(3-cyanopropyl)pyridine (9.6 g) as a yellow solid m.p. 73°–76° C.

(e) Raney nickel moist with ethanol (34 g) was added to a suspension of finely divided 5-bromo-3-nitro-2-(3-cyanopropyl)pyridine (8.4 g) in ethanol (350 ml) under nitrogen. The mixture was cooled (10° C.) and a solution of hydrazine hydrate (2.34 ml) in ethanol (10 ml) was added maintaining the reaction temperature between 12°–15° C. The reaction mixture was allowed to warm to room temperature with constant stirring and hydrazine hydrate (15.5 ml) was added in portions (2.3 ml) in ethanol (3 ml) at regular intervals over 46 hr. Before each addition the reaction mixture was cooled to 15° C. After 23 hr. more Raney nickel (6 g) was added. The reaction was stopped after 47 hr. The catalyst was removed by filtering the reaction mixture through a pad of diatomaceous earth. Evaporation of the solvent yielded an oil (7.9 g) which was chromatographed on a silica column eluting with ethyl acetate/ethanol/0.880 ammonia 15:10:2 to give 3-amino-5-bromo-2-(4-aminobutyl)pyridine (4.0 g) as an oil.

(f) 5-Bromo-2-(4-aminobutyl)-3-aminopyridine (0.5 g) and 2-nitroamino-5-(6-methylpyrid-3-ylmethyl)-4-pyrimidone (0.59 g) were refluxed in pyridine (2 ml) under nitrogen for 9 hours. The pyridine was removed in vacuo and the residual pyridine removed by azeotroping with n-propanol. After chromatography on silica in ethylacetate/ethanol/0.880 ammonia (15:10:2), the residue was crystallised from ethanol-ether and water (2 drops) to give 2-[4-(5-bromo-3-aminopyrid-2-yl)butylamino]-5-(6-methylpyrid-3-ylmethyl) 4-pyrimidone (0.52 g), m.p. 196°–197° C.

EXAMPLE 2

5-Bromo-2-(4-aminobutyl)-3-aminopyridine (0.5 g) and 2-nitroamino-5-(N-oxopyrid-4-ylmethyl)-4-pyrimidone (0.59 g) were refluxed in pyridine (4 ml) under nitrogen for 18 hours. After removal of pyridine in vacuo the residue was re-evaporated with n-propanol, chromatographed in chloroform/methanol (4:1) on silica and crystallised from ethanol to give 2-[4-(5-bromo-3-aminopyrid-2yl)butylamino]-5-(N-oxopyrid-4-ylmethyl)-4-pyrimidone (0.29 g), m.p. 143°–145° C.

EXAMPLE 3

A pharmaceutical composition for oral administration is prepared containing

|   |   | % by weight |
|---|---|---|
| A | 2-[4-(5-bromo-3-aminopyrid-2-yl-butyl-amino]-5-(N—oxopyrid-4-ylmethyl)-4-pyrimidone | 55 |
|   | Dibasic calcium phosphate dihydrate | 20 |
|   | Approved coloring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

What is claimed is:

1. A compound of formula (2):

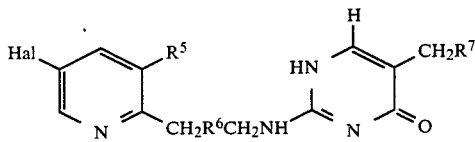

or a pharmaceutically acceptable salt thereof; where
Hal is a halogen atom;
$R^5$ is amino, $C_{1-4}$ alkylamino or $C_{1-4}$ alkanoylamino;
$R^6$ is a $C_{1-3}$ alkylene group; and
$R^7$ is 3-pyridyl; N-oxo-3-pyridyl; 6-methyl-3-pyridyl; N-oxo-6-methyl-3-pyridyl; 6-hydroxymethyl-3-pyridyl; 4,6-dimethyl-3-pyridyl; N-oxo-4,6-dimethyl-3-pyridyl; 6-hydroxymethyl-4-methyl-3-pyridyl; 5,6-dimethyl-3-pyridyl; N-oxo-5,6-dimethyl-3-pyridyl; 6-hydroxymethyl-5-methyl-3-pyridyl; 4-pyridyl or N-oxo-4-pyridyl.

2. A compound according to claim 1 where Hal is bromo.

3. A compound according to claim 1 or claim 2, where $R^5$ is amino.

4. A compound according to claim 1, where $R^6$ is ethane-1,2-diyl.

5. A compound according to claim 1, where $R^7$ is 6-methylpyrid-3-yl or N-oxopyrid-4-yl.

6. A compound according to claim 1 which is 2-[4-(5-bromo-3-aminopyrid-2-yl)butylamino]-5-(6-methylpyrid-3-yl-methyl)-4-pyrimidone or a pharmaceutically acceptable salt thereof.

7. A compound according to claim 1 which is 2-[4-(5-bromo-3-aminopyrid-2-yl)butylamino]-5-(N-oxopyrid-4-yl-methyl)-4-pyrimidone or a pharmaceutically acceptable salt thereof.

8. A hydrochloride salt of a compound of formula (2) according to claim 1.

9. A pharmaceutical composition having histamine $H_1$-antagonist activity comprising an effective amount of a compound according to claim 1 and a pharmaceutically acceptable carrier.

10. A method of blocking histamine $H_1$-receptors which comprises administering to a subject an effective amount to block said receptors of a compound according to claim 1.